United States Patent
Yasunaga et al.

[11] Patent Number: 5,748,366
[45] Date of Patent: May 5, 1998

[54] SURGICAL MICROSCOPE

[75] Inventors: Koji Yasunaga; Hiroshi Fujiwara, both of Hachioji; Masami Hamada, Akishima; Takashi Fukaya; Masahiko Kinukawa, both of Sagamihara; Tomonori Ishikawa; Masanori Kaneda, both of Hachioji; Takeshi Okada, Ina, all of Japan

[73] Assignee: Olympus Optical Co., Ltd., Tokyo, Japan

[21] Appl. No.: 578,386

[22] Filed: Dec. 26, 1995

Related U.S. Application Data

[63] Continuation of Ser. No. 238,693, May 5, 1994, abandoned.

[30] Foreign Application Priority Data

May 7, 1993 [JP] Japan .................. 5-106427
Oct. 22, 1993 [JP] Japan .................. 5-264787

[51] Int. Cl.$^6$ .............. G02B 21/00; G02B 21/36; G02B 21/26; G02B 21/06
[52] U.S. Cl. .............. 359/368; 359/384; 359/363; 359/392; 359/393; 359/389; 359/385; 359/387
[58] Field of Search .............. 359/368, 384, 359/363, 392, 393, 389, 385, 387

[56] References Cited

U.S. PATENT DOCUMENTS

| | | | |
|---|---|---|---|
| 4,362,355 | 12/1982 | Takahashi | 359/393 |
| 4,867,405 | 9/1989 | Nakamura . | |
| 4,871,245 | 10/1989 | Ishikawa et al. | 359/363 |
| 4,881,709 | 11/1989 | Nakamura . | |
| 5,074,651 | 12/1991 | Nagamine | 359/368 |
| 5,173,802 | 12/1992 | Heller | 359/384 |
| 5,173,803 | 12/1992 | Heller | 359/384 |
| 5,205,522 | 4/1993 | Nakamura | 359/384 |
| 5,271,592 | 12/1993 | Lugwig | 359/384 |

Primary Examiner—Paul Dzierzynski
Assistant Examiner—Mohammad Y. Sikder
Attorney, Agent, or Firm—Finnegan, Henderson, Farabow, Garrett & Dunner, L.L.P.

[57] ABSTRACT

To provide a surgical microscope comprising a microscope collimator for enabling the operator to easily recognize the swivel center of the microscope body regardless of what position the microscope body moves for easy setting of the swivel center point of the microscope body, a surgical microscope pivotally supporting a microscope body having, an observation optical system with one point on an observation optical axis of the microscope body as the swivel center. The surgical microscope comprises index projectors as swivel center visible indicators being capable of recognizing the swivel center. This configuration enables the operator to easily recognize the swivel center of the microscope body for easy setting of the swivel center point of the microscope body. Also, to provide a surgical microscope which does not disturb an operator who handles the microscope or performs an operation and also enables the operator to easily observe at every angle from every direction for improving operability, the surgical microscope is capable of changing an observation angle and an observation direction with a gaze point P on an observation optical axis a of a microscope body having an observation optical system as a rotation center. A base unit that can be moved in X, Y, and Z directions is disposed at a position relative to the microscope body and a swivel base rotatable with the gaze point P as a rotation center is installed above the base unit.

7 Claims, 12 Drawing Sheets

SURGICAL MICROSCOPE

This application is a continuation of Ser. No. 08/238,693 filed May 5, 1994 now abandoned.

BACKGROUND OF THE INVENTION

This invention relates to a surgical microscope whose microscope body having an observation optical system, which enables the operator to observe the part to be or being operated on an enlarged scale, can be pivoted with one point on an observation optical axis as the center. Also, this invention relates to a surgical microscope whose microscope body having an observation optical system, which enables the operator to observe the part to be or being operated on an enlarged scale, can be pivoted with one point on an observation optical axis as the center.

Recently, a microscopic operation or microsurgery has been often performed as development of operation methods and surgical instruments. For the microsurgery, a surgical microscope comprising a microscope body having an observation optical system for observing the part to be or being operated on shown on an enlarged scale is used as in ophthalmologic or cerebral surgery.

A general surgical microscope comprises a microscope body comprising a microscope for observing the part to be or being operated on an enlarged scale and a microscope supporter for moving the microscope body to a desired position at a desired angle and holding it. Diversified microscope bodies and microscope supporters are available depending on how operation or what operation is performed.

To meet demand for seeing the observation parts quickly from various angles, namely, for changing the observation angle with the center of a visual field of observation on a focal plane, which will be hereinafter referred to as a "gaze point," as the center, surgical microscopes whose observation angles can be changed by inclining a microscope body with a gaze point as the center have been proposed in Swiss Patent No. 482439 and Japanese Patent Publication Nos.Sho 49-9378 and Hei 3-18891.

With the surgical microscopes described in Swiss Patent No. 482439 and Japanese Patent Publication Nos.Sho 49-9378 and Hei 3-18891, motion of a support rod movable with one point as the center is transmitted via a link mechanism to the microscope body, which can then be moved with the gaze point as the center.

However, with such surgical microscopes, if an attempt is made to incline a microscope body 121 with a gaze point 120 as the center, when the gaze point 120 is deep, an opening 122 will block the microscope body, as shown in FIG. 1. To prevent the opening 122 from blocking the microscope body, the microscope may have a structure pivotally mounted with opening 122 different from the observation part as the center. Although it can be pivoted with a point different from the gaze point as the center by moving a collimator of the microscope in the prior art, the operator is hard to recognize the point and cannot easily set the point.

On the other hand, a general surgical microscope comprises a microscope body comprising a microscope for observing the part to be or being operated on an enlarged scale and a rack section comprising an arm rack for moving the microscope body to a desired position at a desired angle and holding it. Rack sections moving in various manners have been designed with advanced technology of surgery.

For example, a surgical microscope whose focus is positioned on an extension connecting both base ends of an arm comprising a parallel link mechanism is disclosed in Japanese Patent Laid-Open No.Sho 63-296743. Since the part to be or being operated on can be observed at various angles from various directions with focus fixed to one point, i.e., a gaze point, it can be observed at an optimum angle from an optimum direction. Similar surgical microscopes are described in the above-described Japanese Patent Publication No.Sho 49-9378, U.S. Pat. No. 4,881,709, the above-described Swiss Patent No. 482439.

However, to rotate a microscope body with a gaze point as the center, conventional surgical microscopes require that an arm supporting the microscope body be formed with a complicated mechanism. The mechanism, which is near the part to be or being operated on, disturbs the operator who handles the microscope body in the operation.

SUMMARY OF THE INVENTION

It is therefore an object of the invention to provide a surgical microscope to enable the operator to easily recognize the swivel center of a microscope body.

To the end, according to the invention, there is provided a surgical microscope having a microscope body having an observation optical system which is capable of changing an observation direction with one point on an observation optical axis of the microscope body as the swivel center, the surgical microscope comprising swivel center visible means being capable of recognizing the swivel center.

This configuration enables the operator to easily recognize the swivel center of the microscope body for easy setting of the swivel center point of the microscope body.

It is another object of the invention to provide a surgical microscope which has a support mechanism such as arms supporting a microscope body not disturbing an operator who handles the microscope body or performs an operation and also enables the operator to change an observation angle or an observation direction with the gaze point as the center for easy operation.

To the end, according to the invention, there is provided a surgical microscope capable of changing an observation angle and an observation direction with a gaze point on an observation optical axis of a microscope body having an observation optical system as a rotation center, the surgical microscope comprising rotation drive means with the rotation center as a reference at a position relative to the microscope body.

Thus, the mechanism as rotation drive means for changing the observation angle and direction with the gaze point as the center is disposed at a position distant from the microscope body, thus does not disturb the operator who handles the microscope body and performs the operation and also enables the operator to easily observe the part to be or being operated on at every angle from every direction.

DESCRIPTION OF THE PREFERRED EMBODIMENTS

Referring now to the accompanying drawings, there are shown preferred embodiments of the invention.

Figure 1:
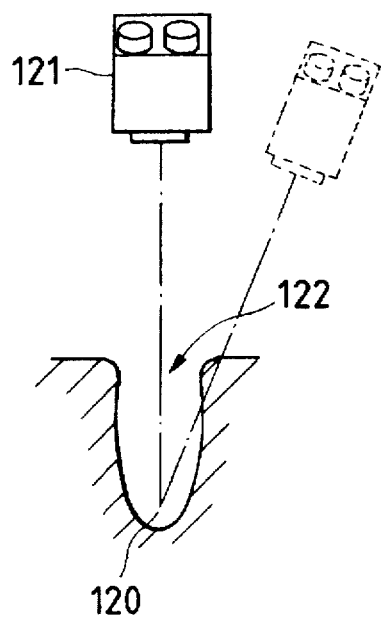
FIG. 1 is an illustration of function of a conventional surgical microscope.
Figure 2:
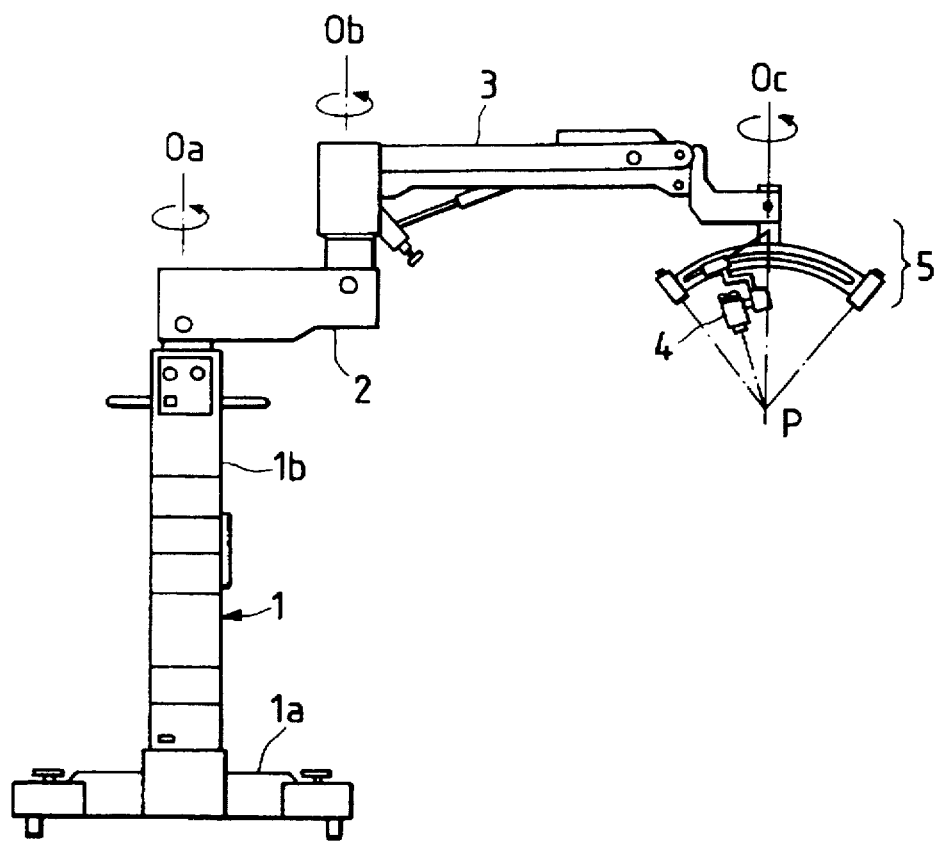
FIG. 2 is a schematic structural drawing of a surgical microscope according to a first embodiment of the invention.
Figure 3:
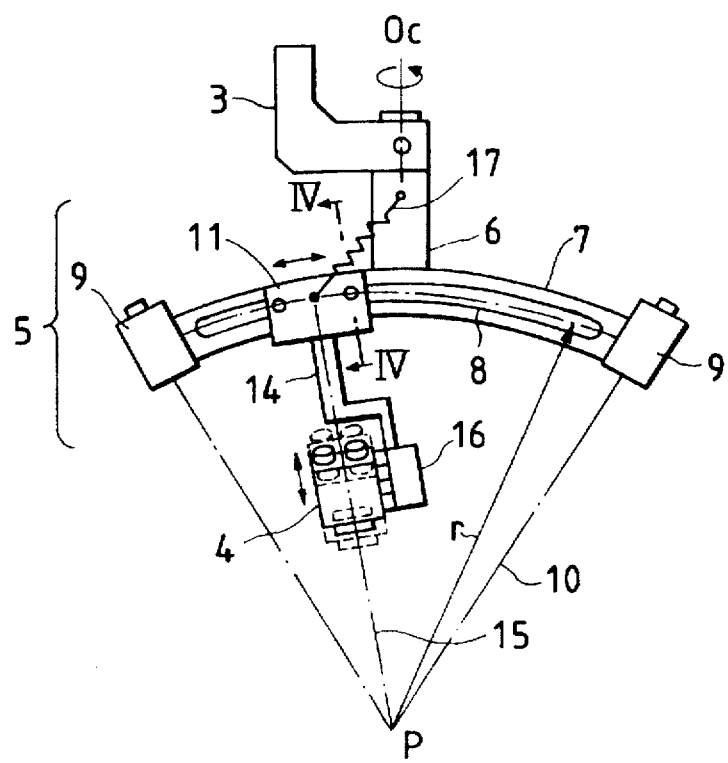
FIG. 3 is a structural drawing of a microscope body and a second arm in the first embodiment.
Figure 4:
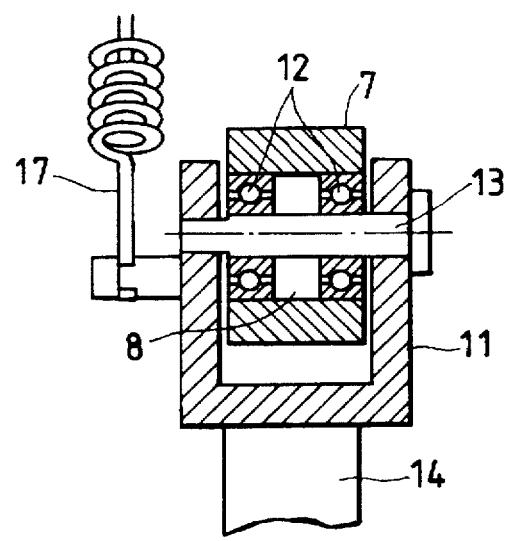
FIG. 4 is a sectional view taken on line IV—IV of FIG. 3.
Figure 5:
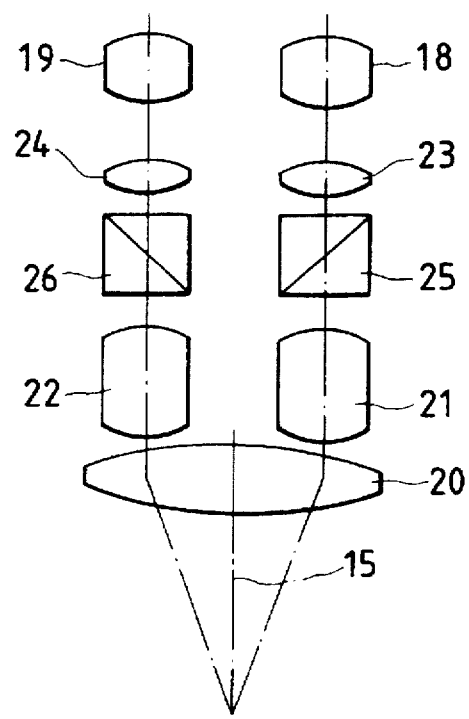
FIG. 5 is a structural drawing of an optical system of the microscope body in the first embodiment.
Figure 6:
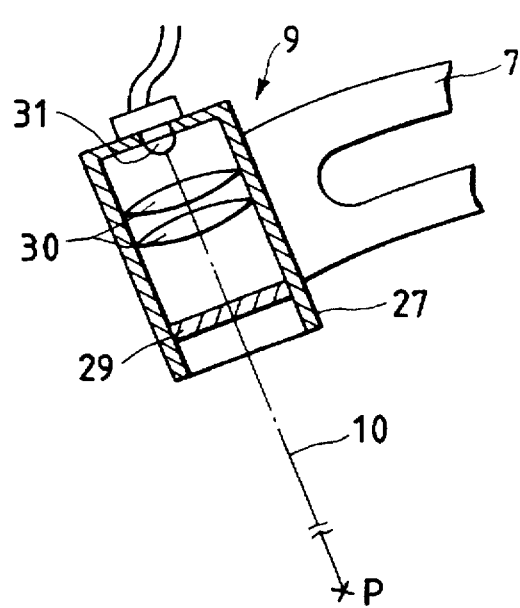
FIG. 6 is a structural drawing of an index projector in the first embodiment.
Figure 7:
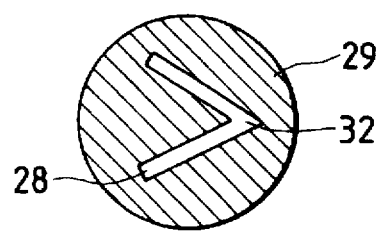
FIG. 7 is a drawing showing the form of a douser in the index projector in the first embodiment.

FIGS. 2 to 9 show a first embodiment of the invention. FIG. 2 is a schematic structural drawing of a surgical microscope according to the first embodiment of the invention. FIG. 3 is a structural drawing of a microscope body and a second arm in the first embodiment. FIG. 4 is a partial sectional view of the second arm. FIG. 5 is a structural drawing of an optical system of the microscope body. FIG. 6 is a structural drawing of an index projector. FIG. 7 is a drawing the form of a douser in the index projector. FIGS. 8a to 8c and 9 are drawings showing the index forms.

Rack 1 shown in FIG. 2 is movable on a floor and consists of a base 1a and a support 1b disposed vertically to the base 1a. One end of a first arm 2 containing a light source (not shown) is pivotally mounted on the top of the support 1b with an axis Oa with the center, and one end of a swivel pantograph arm 3 with an axis Ob with the center is mounted on the other end of the first arm 2. A swivel second arm 5 with an axis Oc as the center for supporting a microscope body 4 is mounted on the other end of the pantograph arm 3.

At the second arm 5 shown in FIG. 3, numeral 6 is a supporting rod, one end of which is pivotally mounted on the pantograph arm 3 with the axis Oc as the center. A circular arm 7 is fixed to the other end of the supporting rod 6. The circular arm 7 is formed with a guide groove 8 on a circular arc having radius r with point P on an observation optical axis 15 of the microscope body 4 described below as the center, and index projectors 9 are disposed on either end of the circular arm 7 at an angle at which a projection optical axis 10 matches the point P.

FIG. 4 is a sectional view taken on line IV—IV of FIG. 3, wherein numeral 11 is a U support member which supports a support axis 13 for pivotally supporting two rollers 12 inserted in the guide groove 8 and movable therein.

A microscope body support arm 14 is mounted to the U support member 11 and the microscope body 4 is installed on the microscope body support arm 14. The junction part of the microscope body support arm 14 and the microscope body 4 is formed as a microscope collimator 16 capable of moving the microscope body 4 in the direction of the observation optical axis 15 by a motor (not shown)(see FIG. 3). The U support member 11 and the supporting rod 6 are connected by a tension spring 17.

Next, the structure of an optical system of the microscope body 4 shown in FIG. 5 is described. A pair of observation optical systems comprises an object lens 20, a pair of zoom lenses 21 and 22, and a pair of image lenses 23 and 24 in front of eyepieces 18 and 19 disposed in order from an object.

A beam splitter 25 is disposed between the zoom lens 21 and the image lens 23 and a beam splitter 26 is disposed between the zoom lens 22 and the image lens 24 on each observation optical path. The microscope body 4 is designed so that the center of a visual field of observation on the focal plane of the optical system matches point P when the microscope collimator 16 is at a reference position.

Figure 8A:
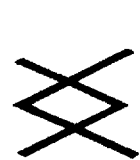
FIGS. 8a, 8b and 8c are drawings showing the index forms in the first embodiment.
Figure 8B:
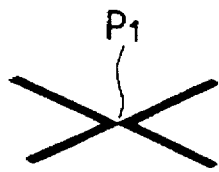

Next, the structure of the index projector 9 is described with reference to FIG. 6, wherein numeral 27 is a housing connected to the circular arm 7. The housing 27 contains a douser 29 having a light beam transmission area 28 of the form shown in FIG. 7, beam expanders 30, and a semiconductor laser 31 for emitting red light of a visible region disposed in order from point P. The two index projectors 9 installed symmetrically to the axis Oc are connected to the circular arm 7 at a predetermined angle so that when indexes projected through the dousers 29 are projected on a substantially horizontal plane containing the point P, they become as shown in FIG. 8b. At the same time, the index projectors 9 are disposed so that the tip 32 of the light beam transmission area 28 of the douser 29 of one index projector is opposite to that of the other index projector and that the projected images match at the point P.

Next, the operation of the surgical microscope having the above-mentioned structure is described. When the microscope collimator 16 of the microscope body 4 is at a reference position, the center of a visual field of observation on the focal plane is designed to match the center point P of the circular arc forming the guide groove 8 of the circular arm 7. Thus, in FIG. 3, the microscope body 4 can be rotated in the paper face direction with the point P as the center when the microscope collimator 16 is at the reference position.

At the time, when the microscope body 4 inclines with respect to the vertical axis, the tension spring 17 located between the U support member 11 and the supporting rod 6 stretches, offsetting force received in the inclination direction of the microscope body 4 by gravity for balancing so that the microscope body 4 does not naturally move even if it inclines at any angle.

The supporting rod 6 supports the circular arm 7 and is pivotally connected to the pantograph arm 3 with the axis Oc as the center. Thus, the microscope body 4 makes spherical motion with the point P as the center by combining rotary motion to the left or right with the point P as the center by the circular arm 7 and swivel motion with the axis Oc as the center.

Figure 8C:

Next, index projection is described. In FIG. 6, flux of laser light emitted from the semiconductor laser 31 in the index projector 9 is expanded by the beam expanders 30 and passes through the light beam transmission area 28 of the douser 29, thereby projecting the form of the light beam transmission area 28 as parallel light toward the point P. The relationship among projected images depending on the object or projection face position for the point P is shown in FIGS. 8a, 8b and 8c. FIG. 8a shows an example in which the object exists on the farther point side than the point P; FIG. 8b shows an example in which the object matches the point P; and FIG. 8c shows an example in which the object exists on the nearer point side than the point P.

While checking the positional relationship between the two projected indexes, the operator moves the microscope body 4 and the second arm 5 as a whole horizontally or up and down by means of the first arm 2 and the pantograph arm 3 so that the index form becomes as shown in FIG. 8b and that the swivel center point of the microscope body 4 indicated as a contact of the two indexes is set to the target point.

Then, while seeing the object through the eyepieces 18 and 19, the operator adjusts the focus of the lenses so that the observation image can be made sharp by means of the microscope collimator 16. Normally, the swivel center position of the microscope body 4 at which the operator aims is the center of the visual field of the observation part or the center of an opening near the microscope body 4 from the observation part.

Figure 9:
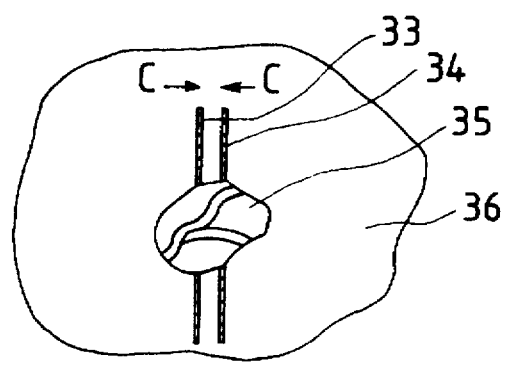
FIG. 9 is a drawing showing the index form in the first embodiment.

For the former, the swivel center of the microscope body 4 can be set to the target part. The latter is required to observe the inside of a hole through a small opening, in which case the operator matches the swivel center of the microscope body 4 to tissue near the opening (in many cases, body surface) according to a similar procedure to the former and moves the microscope body 4 in substantially parallel to the object surface so that the center of the opening matches the center of the visual field while seeing through the eyepieces 18 and 19 of the microscope body 4. Then, the operator may focus the microscope on the observation part by means of the microscope collimator 16 matching the depth of the observation part from the opening. If indexes projected from the two index projectors 9 are made vertical line indexes 33 and 34 to the observation direction of the operator and the line indexes 33 and 34 are aligned as they overlap each other at the swivel center point P of the microscope body 4, as shown in FIG. 9, the operator can set the swivel center to an opening 35 by moving the line indexes 33 and 34 in the arrow directions C around the opening 35 (body surface) for overlapping the line indexes.

If the swivel center of the microscope body 4 is on space, an index may be inserted mechanically in the swivel center point of the microscope body 4 for enabling the operator to make visual inspection directly. As the structure, a fixed arm 41 extending in the observation direction is disposed on the microscope body support arm 14 and an expansion pipe 42 is mounted to the tip of the fixed arm 41, as a modified form of the first embodiment shown in FIG. 10. The expansion pipe 42 comprises a plurality of pipes different in diameter for expansion and has a stopper (not shown). The expansion pipe 42 has a ball 43 at the tip of the innermost pipe.

The length of the expansion pipe 42 and the connection angle to the fixed arm 41 are determined so that the ball 43 matches the swivel center point P of the microscope body 4 when the expansion pipe 43 is expanded to the longest. The expansion operation can be driven by a motor by turning on or off a switch.

Therefore, as required, the operator can introduce the ball 43 to the swivel center point P of the microscope body 4 and move the ball 43 and the microscope body 4 as a whole to the target part for easily setting the swivel center of the microscope body 4 even on space. Such an index insertion system is not limited to the expansion pipe 42 and the ball 43 described above.

According to the modified embodiment, the operator can make direct visual inspection of the swivel center of the microscope body 4 without seeing the microscope body 4. The operator can recognize that the swivel center point P of the microscope body 4 shifts forward or backward from the target part from the positional relationship between two projected indexes, or can use line indexes to set the swivel center point P on the space of the opening 35 for quick setting.

Figure 10:
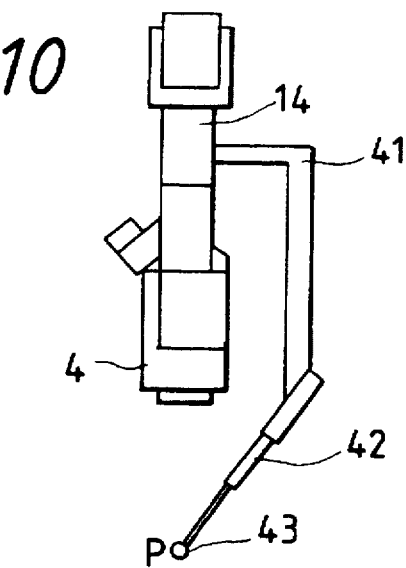
FIG. 10 shows a modified form of the first embodiment and is a structural drawing for inserting an index mechanically.
Figure 11:
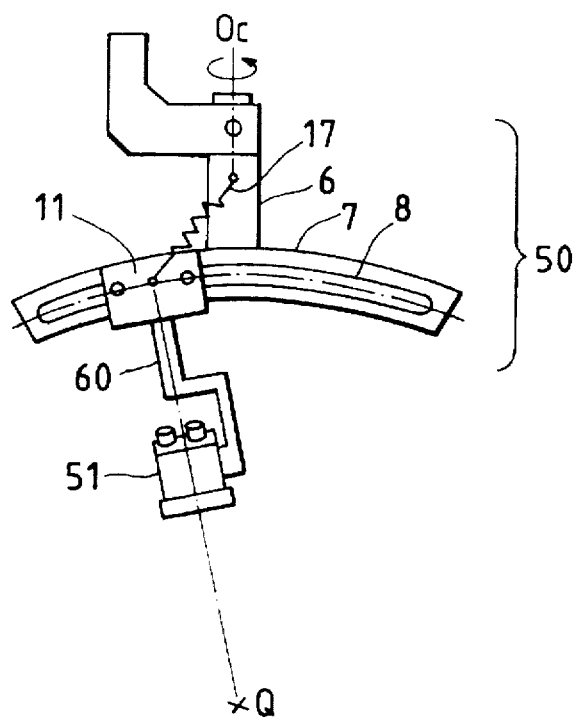
FIG. 11 is a structural drawing of a second arm of a surgical microscope according to a second embodiment of the invention.
Figure 12:
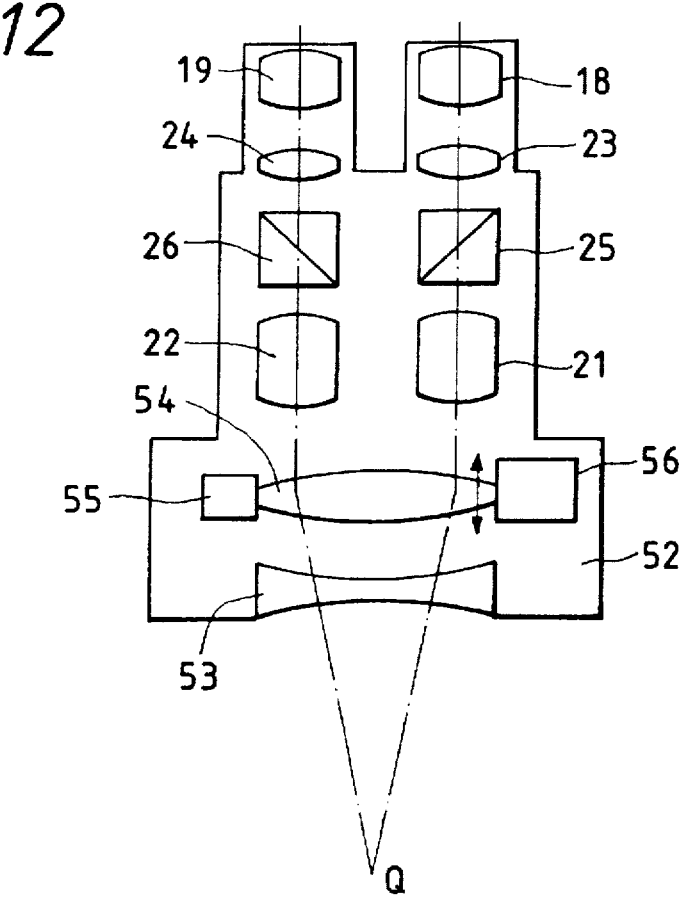
FIG. 12 is a structural drawing of an optical system of a microscope body in the second embodiment.
Figure 13:
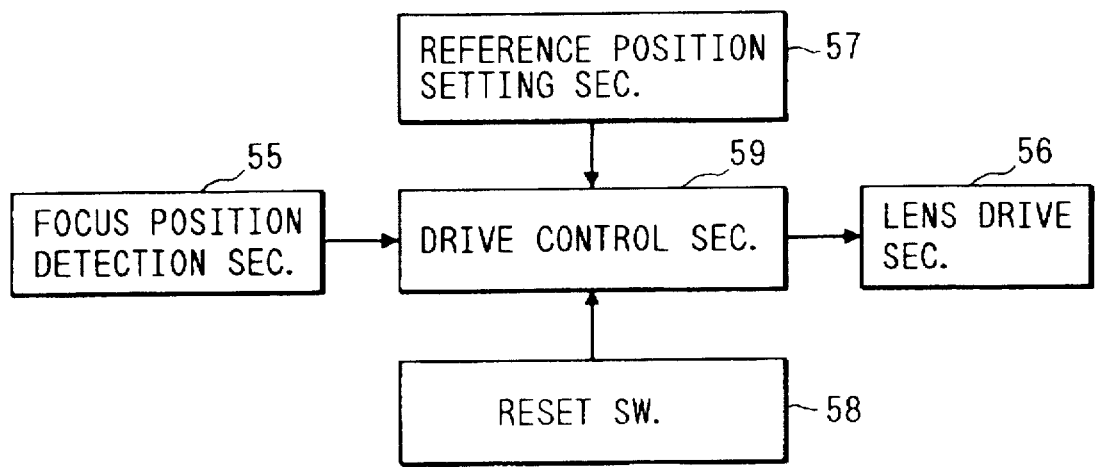
FIG. 13 is a block diagram showing the configuration of an electric system in the second embodiment.

FIGS. 11 to 13 show a second embodiment of the invention. FIG. 10 is a structural drawing of a second arm of a surgical microscope according to the second embodiment. FIG. 12 is a structural drawing of an optical system of a microscope body. FIG. 13 is a block diagram showing the configuration of an electric system.

In FIG. 11, a second arm 50 has the same structure as the second arm 5 in the first embodiment except that it does not contain the index projectors 9 on the end of circular arm 7 or the microscope collimator 16, that a microscope body support arm 60 and a microscope body 51 are connected, that the microscope body 51 is formed with a variable focus object lens 52, or that the microscope body 51 is supported so that the center point of the circular arm 7 is matched to the center point Q of a visual field on a focal plane on the object side at a reference focus distance of the microscope body 51 described below, for example, at the shortest focus distance.

Next, the structure of an optical system of the microscope body 51 shown in FIG. 12 is described. A pair of observation optical systems comprises a variable focus object lens 52, a pair of zoom lenses 21 and 22, and a pair of image lenses 23 and 24 in front of eyepieces 18 and 19 disposed in order from an object. A beam splitter 25 is disposed between the zoom lens 21 and the image lens 23 and a beam splitter 26 is disposed between the zoom lens 22 and the image lens 24 on an observation optical path.

The variable focus object lens 52 consists of a fixed concave lens 53 and a movable convex lens 54 in order from the object. The movable convex lens 54 has a focus position detection section 55 and a cum shaft (not shown) rotated by a motor and is connected to a lens drive section 56 that can move the movable convex lens 54 in the optical axis direction.

Next, the configuration of an electric system shown in FIG. 13 is described. In FIG. 13, numeral 57 is a reference position setting section for previously initializing the reset position of the variable focus object lens 52, numeral 55 is the focus position detection section for detecting the position of the variable focus object lens 52, numeral 58 is a reset switch for outputting a reset signal, and numeral 56 is the lens drive section for driving the variable focus object lens 52, which are connected to a drive control section 59.

Next, the operation of the surgical microscope according to the second embodiment is described. Before an operation, first, position data of the movable convex lens 54 of the variable focus object lens 52 when normally the focus distance of the microscope body 51 by the variable focus object lens 52 becomes the shortest is input to the reference position setting section 57 and is stored in a memory (not shown) of the drive control section 59.

Next, when the reset switch 58 of a grip (not shown) attached to the microscope body 51 is pressed, the drive control section 59 calculates the position of the movable convex lens 54 of the variable focus object lens 52 in response to information from the focus detection section 55 and compares it with the position information of the movable convex lens 54 previously stored in the memory, then outputs a drive signal to the lens drive section 56 for moving the movable convex lens 54 of the variable focus object lens 52 so as to focus on the center point Q of the visual field on the focal plane on the object side at the reference focus distance of the microscope body 51, in the embodiment, when the focus distance is the shortest.

When the operation terminates, the microscope body 51 can be pivoted with the point Q as the center as in the first embodiment.

While seeing through the eyepieces 18 and 19 of the microscope body 51, the operator moves the microscope body 51 and the second arm 50 as a whole horizontally or up and down by means of the first arm 2 and the pantograph arm 3 so that the swivel center point Q of the microscope body 51, namely, the center of the visual field of observation on the focal plane is set to the target part.

In a technique of approaching the deep part of brain in order from its surface in cerebral surgery, the swivel center point Q of the microscope body 51 is once set on the surface of brain, etc., and as the operation advances to the deep part of brain, the movable convex lens 54 of the variable focus object lens 52 may be moved in a direction to extend the focus distance by a foot switch (not shown) for focusing on the operation field. Even in the condition, the swivel center of the microscope body 51 is fixed to the surface of brain.

Although the variable focus object lens 52 is used as a collimator in the second embodiment, it can also be embodied by disposing focus position detection section 55 and motor in microscope collimator 16 at a surgical microscope comprising a microscope collimator 16 for driving the entire microscope body 4 as shown in the first embodiment, needless to say.

According to the second embodiment, the variable focus object lens 52, which is a collimator indispensable to a surgical microscope, is driven to the reference position, thereby making the swivel center point Q of the microscope body 51 visible, thus the surgical microscope can be miniaturized as a simple structure without need for special means.

Figure 14:
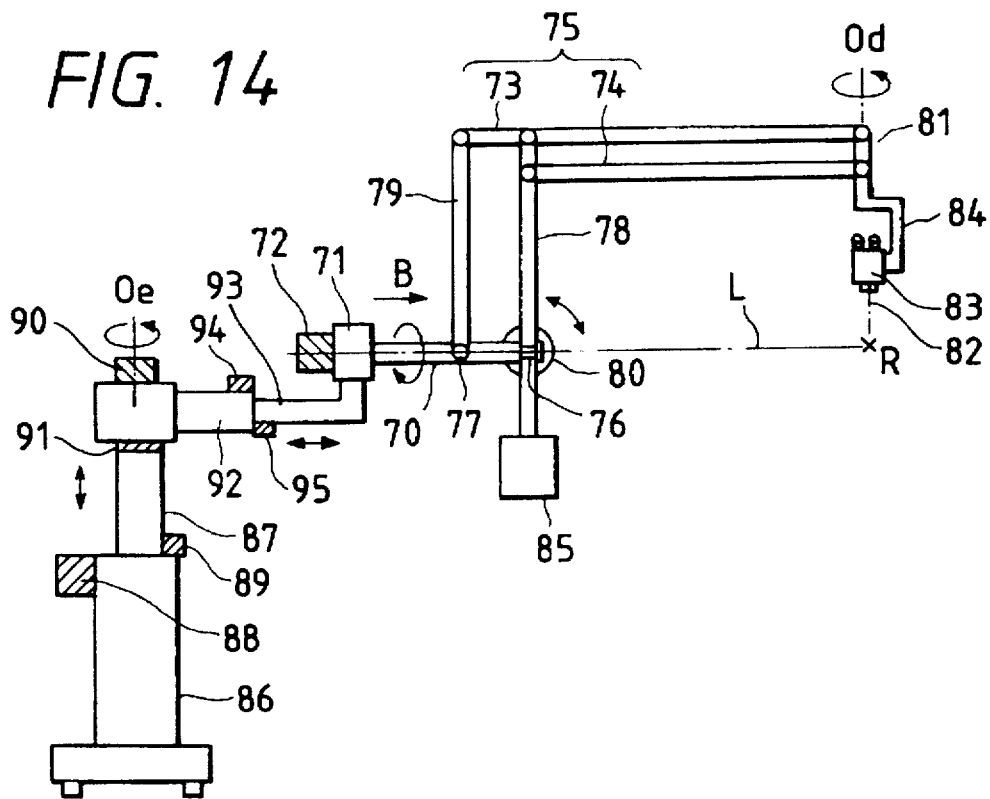
FIG. 14 is a general structural drawing of a surgical microscope according to a third embodiment of the invention.
Figure 15:
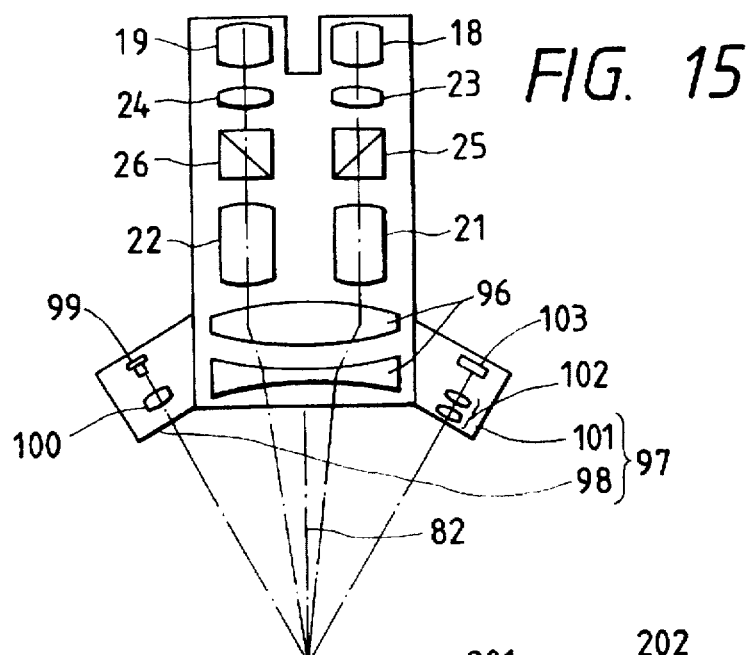
FIG. 15 is a structural drawing of an optical system of a microscope body in the third embodiment.
Figure 16:
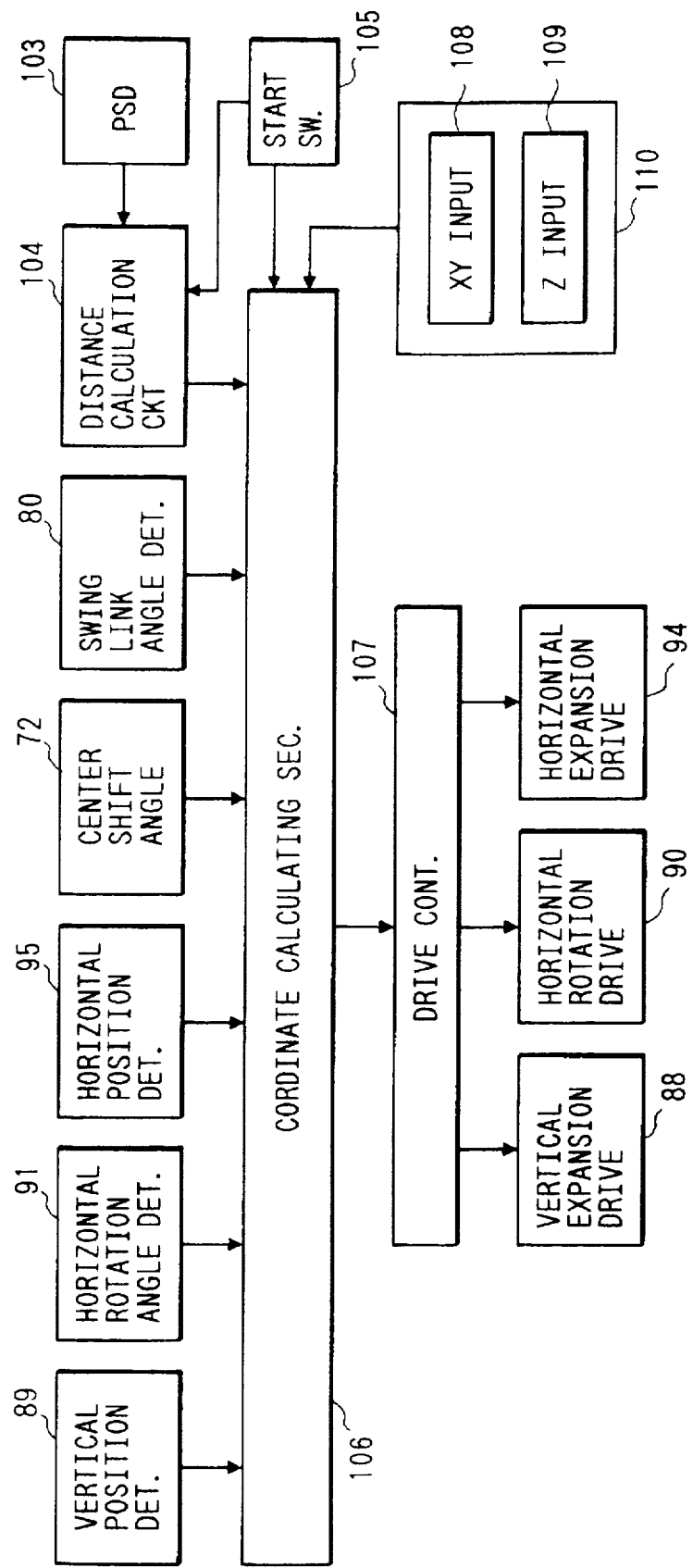
FIG. 16 is a block diagram showing the configuration of an electric system in the third embodiment.

FIGS. 14 to 16 show a third embodiment of the invention. FIG. 14 is a general structural drawing of a surgical microscope according to the third embodiment of the invention. FIG. 14 is a structural drawing of an optical system of a microscope body. FIG. 16 is a block diagram showing the configuration of an electric system.

In FIG. 14, numeral 70 is a center shaft which is pivotally supported via a bearing (not shown) in a holding member 71. The holding member 71 is formed with a center shaft angle detection section 72 for detecting the rotation angle of the center shaft 70.

A parallel link mechanism 75 consisting of a first parallel link 73 and a second parallel link 74 is secured on the front side of the center shaft 70 (in the B direction in FIG. 14). The first parallel link 73 comprises base ends 76 and 77 pivotally mounted to the center shaft 70 and two swing link members 78 and 79 swingable with the base ends 76 and 77 as the center. The base end 76 is formed with a swing link angle detection section 80 for detecting the rotation angle of the swing link member 78.

The second parallel link 74 is attached to one end of the swing link member 78 and is pivoted in association with the first parallel link 73. The tip 81 of the second parallel link 74 swings in parallel with the swing link members 76 and 77, and a microscope body 83 is supported by a microscope body support arm 84 below the tip 81 so that a rotation axis Od and an observation optical axis 93 are on the same axis.

At the time, the observation optical axis 82 of the microscope body 83 crosses an extension connecting the base ends 76 and 77 of the parallel link mechanism 75, namely, axial center extension of the center shaft 70, L, at point R.

The swing link member 78 is also extended to the opposite side to the base end 76 and the end of the extension is formed with a balancer plumb 85 for balancing the parallel link mechanism 75, the microscope body support arm 84, the center shaft 70 of the microscope body 83, and a pivot with the base end 76 as the center. Numeral 86 is a rack which contains a vertical expansion drive section 88 containing a motor (not shown) capable of expanding a vertical expansion arm 87 up and down by electric power and a vertical position detection section 89 for detecting the position of the vertical expansion arm 87 in the move direction.

The top of the vertical expansion arm 87 is formed with a horizontal arm 92 comprising a horizontal rotation drive section 90 containing a motor (not shown) capable of pivoting by electric power with an axis Oe as the center and a horizontal rotation angle detection section 91 for detecting a rotation angle.

A horizonal expansion arm 93 is disposed on the other end of the horizontal arm 92, and a horizontal expansion drive section 94 having a motor (not shown) capable of expanding the horizontal expansion arm 93 in the axial direction of the horizontal arm 92 and a horizontal position detection section 95 for detecting the position of the horizontal expansion arm 93 in the expansion direction are disposed. The holding member 71 for holding the center shaft 70 is attached to the tip of the horizontal expansion arm 93.

Next, the structure of the microscope body 83 is described with reference to FIG. 15. In the figure, numeral 96 is a variable focus object lens which is the same as the variable focus object lens in the second embodiment except that it does not contain the focus position detection section 55 in the second embodiment. Parts identical with those previously described with reference to FIG. 12 are denoted by the same reference numerals in FIG. 14 and will not be discussed again. A distance detection section 97 for calculating a distance by trigonometrical survey is disposed on the wall of the microscope body 83. A floodlight section 98 of the distance detection section 97 consists of a light emitting device 99 for emitting a pulse light beam to an object and a condensing lens 100 for gathering light emitted from the light emitting device 99 like a spot. A light receiving section 101 comprises PSD 103 for detecting light reflected from the object through a reduction optical system 102.

Next, the configuration of an electric system of the surgical microscope is discussed with reference to FIG. 16. In the figure, numeral 104 is a distance calculation circuit connected to the PSD 103 and a start switch 105. Numeral 106 is a coordinate calculation section responsive to signals input from the distance calculation circuit 104, the vertical position detection section 89, the horizontal position detection section 95, the horizontal rotation angle detection section 91, the center shaft angle detection section 72, the swing link angle detection section 80, and the start switch 105 for calculating three-dimensional coordinates of the center of a visual field of observation.

Numeral 107 is a drive control section responsive to a signal from the coordinate calculation section 106 for outputting a drive signal to the vertical expansion drive section 88, the horizontal rotation drive section 90, an the horizontal expansion drive section 94 connected thereto. A foot switch 110 having an XY input section 108 for driving the surgical microscope in a horizontal plane and a vertical input section 109 for vertical movement is connected to the drive control section 107.

Next, the operation of the surgical microscope according to the third embodiment is described. First, a pivot of the microscope body 83 is discussed. In FIG. 14, for an inclination within the paper face of the microscope body 83, namely, in the direction along the parallel link mechanism 75, crosspoint P of the observation optical axis 82 of the microscope body 83 and the extension L connecting both the base ends 76 and 77 of the parallel link mechanism 75, namely, the axial center extension of the center shaft 70 remains fixed to one point even if the parallel link mechanism 75 is deformed. At the time, the balancer plumb 85 attached to the other end of the swing link member 78 also pivots with the base end 76 as the center by an angle of degrees in response to deformation of the parallel link mechanism 75. Therefore, weight of the parallel link mechanism 75 and the microscope body 83 is offset by the balancer plumb 85 for automatically maintaining a weight balance.

An inclination in the paper face vertical direction of the microscope body 83 can be made by rotating the microscope body 83 and the parallel link mechanism 75 as a unit with the center shaft 70 as the center. At the time, the balancer plumb 85 also rotates in the opposite direction to the inclination direction of the parallel link mechanism 75 and the microscope body 83 for maintaining a weight balance. A pivot can be executed with the focus R as the center by combining inclinations of the parallel link mechanism 75 and in the paper face direction and paper face vertical direction of the microscope body 83.

To move the microscope body 83 to the target part during operation, the operator handles the XY input section 108 and vertical input section 109 of the foot switch 110. A signal from the foot switch 110 is input to the drive control section 107, which then output drive signals converted into motion in each direction to the vertical expansion drive section 88, the horizontal rotation drive section 90, and the horizontal expansion drive section 94. Therefore, the microscope body 83 moves as a unit with the parallel link mechanism 75. While seeing through the eyepieces 18 and 19 of the microscope body 83, the operator positions the swivel center point of the microscope body 83 in the center of the observation visual field obtained through the observation optical system of the microscope body 83. At the time, the focus by the variable focus object lens 95 need not match the center of the visual field.

Next, when the operator turns on the start switch 105, the distance calculation circuit 104 and the coordinate calculation section 106 are started and a pulse light beam is emitted to the object through the condensing lens 100 from the light emitting device 99 of the floodlight section 98. The light reflected from the object is projected through the reduction optical system 102 to the PSD 103 as a spot, and the position of center of gravity of the spot is detected.

The center-of-gravity position of the spot is output from the PSD 103 to the distance calculation circuit 104, which then calculates the distance from the microscope body 83 to the object. Further, the coordinate calculation section 106 calculates the coordinates of the base end 76 of the parallel link mechanism 75 in response to the signals from the vertical position detection section 89, the horizontal position detection section 95, and the horizontal rotation angle detection section 91. When the coordinates of the base end 76 are calculated, the coordinates of the point R of the axial center extension of the center shaft 70 and the observation optical axis 82 of the microscope body 83 are calculated.

Further, the coordinate calculation section 106 calculates the coordinates of the microscope body 83 and those of the object positioned in the center of the observation visual field in response to the signals from the center shaft angle detection section 72, the swing link angle detection section 80, and the distance calculation circuit 104. Then, the coordinate calculation section 106 finds the difference between the coordinates of the crosspoint R and those of the object, and outputs data of the XYZ directions to the drive control section 107.

In response to the data of the XYZ directions, the drive control section 107 outputs drive signals to the vertical expansion drive section 88, the horizontal rotation drive section 90, and the horizontal expansion drive section 94 for driving the vertical expansion arm 87, the horizontal arm 92, and the horizontal expansion arm 93, whereby the crosspoint R of the axial center extension of the center shaft 70 and the observation optical axis 82 of the microscope body 83 matches the object position in the center of the observation visual field of the microscope body 83.

Now, the microscope body 83 can be pivoted with the object surface existing on the center of the observation visual field (observation optical axis 82) as the center. Then, the operator may drive the variable focus object lens 96 to focus on the target part for observation. If the swivel center point of the microscope body 83 is a space such as an opening, the operator may once set the swivel center point of the microscope body 83 on tissue near the opening as in the first embodiment, and drive the vertical expansion arm 87, the horizontal arm 92, and the horizontal expansion arm 93 by handling the foot switch 110 for moving the microscope body 83 in substantially parallel to the object surface for positioning the opening in the center of the observation visual field.

According to the embodiment, to set the swivel center of the microscope body 83, the microscope body 83 is simply moved so that the swivel center point of the microscope body 83 comes to the center of the visual field, thereby automatically setting the swivel center point of the microscope body 83 regardless of the focus. That is, the operator need not focus on the swivel center point of the microscope body 83 and can easily set it.

As described above, the surgical microscope of the invention comprises swivel center visual means for enabling the operator to easily recognize the swivel center of the microscope body regardless of what position the microscope body moves for easy setting of the swivel center point of the microscope body.

Figure 17:
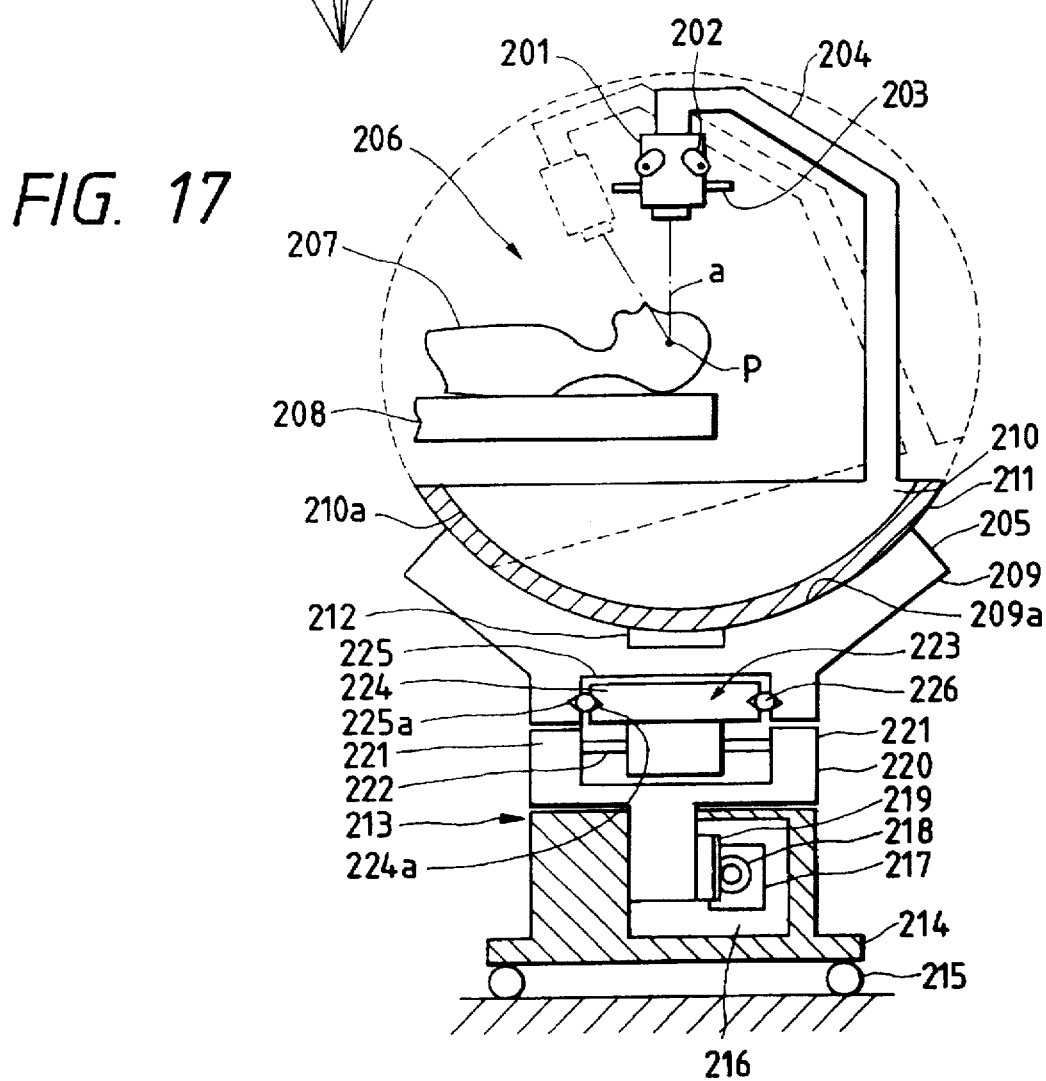
FIG. 17 is a general structural drawing of a surgical microscope according to a fourth embodiment of the invention.

FIG. 17 is a general view of a surgical microscope according to a fourth embodiment of the invention, wherein numeral 201 is a microscope body containing an observation optical system. The microscope body 201 is provided with an eyepiece section 202 and a grip 203 for pivot operation. The microscope body 201 is supported on the top end of an arm 204. The bottom end of the arm 204 is fixed to the fringe of a swivel base 205. That is, the arm 204 is bent so as to keep out of an observation space 206 below the microscope body 201. An operating table or bed 208 on which a patient lies on his or her back can be placed in the observation space 206.

The swivel base consists of a spherical concave member 209 having a concave spherical section 209a on the top face and a spherical convex member 210 having a convex spherical section 210a on the bottom face fitted in the concave spherical section 209a. Further, the center of the spherical radii of the concave spherical section 209a and the convex spherical section 210a matches the focus of the microscope body 201, which will be hereinafter referred to as gaze point P, and the microscope body 201, the grip 203, the arm 204, and the spherical convex member 210 are distributed in weight so that the gaze point P matches the position of center of gravity of the microscope body 201, the grip 203, the arm 204, and the spherical convex member 210.

An iron member 211 is fixed on the surface of the convex spherical section 210a of the spherical convex member 210 and the concave spherical section 209a of the spherical concave member 209 is formed with an electro-magnetic brake 212; when unenergized, the spherical convex member 210 is fixed via the iron member 211; when energized, the spherical convex member 210 can be freed via the iron member 211, thereby fixing the spherical convex member 210 at any desired position after rotation.

Further, the swivel base 205 is supported on a base unit 213 capable of moving it in the X, Y, and Z directions, forming swivel drive section. The base unit 213 comprises a base 214 provided with casters 215 on the bottom. A concave section 216 is located in the upper portion of the base 214. A motor 217 with its rotation shaft turned sideways is fixed within the concave section 216. The motor 217 is turned on and off and rotated forward and reversely by means of a foot switch (not shown). A pinion 218 is fitted in the rotation shaft of the motor 217 and meshes with a rack 219 movable in the vertical direction. The rack 219 is fixed to an elevation member 220 supported on the base 214 in such a manner that it can rise and fall.

A pair of convex parts 221 is formed on both ends of the upper face of the elevation member 220. A second guide shaft 222, which is located between the convex parts 221, is provided with a mobile unit 223 movable in the X direction.

A plate-like support 224 is located on the top of the mobile unit 223. A section 225 consisting of a concave part formed in the lower portion of the spherical concave member 209 is fitted into the support 224. Further, V grooves 224a and 225a along the Y direction are formed on both the outer sides of the support 224 and both the inner sides of the section 225, and a ball 226 for supporting the spherical concave member 209 movable in the Y direction is located between the V grooves 2224a and 225a.

A move of the mobile unit 223 in the X direction and a move of the spherical concave member 209 in the Y direction are driven by a well-known electric-powered drive mechanism (not shown) which is controlled by means of the foot switch. Therefore, the swivel base 205 can be moved in the X, Y, and Z directions by means of the base unit 213, and the microscope body 201 supported via the arm 204 by the swivel base 205 can be rotated in any desired direction with the gaze point P as the supporting point.

Next, the operation of the surgical microscope having the structure described above is discussed.

First, the swivel base 213 is moved in the XY direction so that the part to be operated on of a patient 207 on the operating table 208 can be observed. Observation optical axis a of the microscope body 201 is positioned at the part to be operated on of the patient 207 (gaze point P). In this case, for a move in the X direction, the mobile unit 223 moves for the guide shaft 222; for a move in the Y direction, the spherical concave member 209 moves for the mobile unit 223.

Next, when the motor 217 is driven by handling the foot switch, the elevation member 220 rises or falls for the base 214 by means of the rack meshed with the rotating pinion 218 and the microscope body 201 rises or falls via the swivel base 205. Then, the operator adjusts focus of the microscope body 201 to the gaze point P of the part to be operated on.

Further, to change the observation direction to the gaze point P of the part to be or being operated on, the operator energizes the electromagnetic brake 212 by handling the foot switch to free the spherical convex member 210 via the iron member 211 and takes a grasp on the grip 203 to push or pull the microscope body 201 in any desired direction. Then, the spherical convex member 210 makes spherical motion for the spherical concave member 209 for causing the microscope body 201 to make spherical motion with the gaze point P as the center for changing the observation direction.

At the time, the gaze point P matches the position of the center of gravity of the microscope body 201, the grip 203, the arm 204, and the spherical convex member 210, thus handling force is very light. To rotate the microscope body 201 and then fix it at any desired position for observation, the operator can turn off energization of the electromagnetic brake 212 by handling the foot switch for fixing the iron member 211 of the spherical convex member 210 by the electromagnetic brake 212.

In the fourth embodiment, even if the microscope body 201 is rotated with the gaze point P as the center, the spherical convex member 210, rotation or swivel drive means, is located below the operating table 208 and the arm 204 simply connects the microscope body 201 and the spherical convex member 210, thus the periphery of the microscope body 201 is simplified and does not disturb the operator; good operability is provided. Since the rotation center of the microscope body 201 and the parts rotated together with the microscope body 201 match in center of gravity, the microscope body 201 can be rotated lightly and the lock mechanism such as the electromagnetic brake 212 can be miniaturized. Further, the microscope body 201 can be rotated with the gaze point P as the center without any complicated structure such as conventional link mechanism; the surgical microscope can be provided at low costs.

Figure 18:
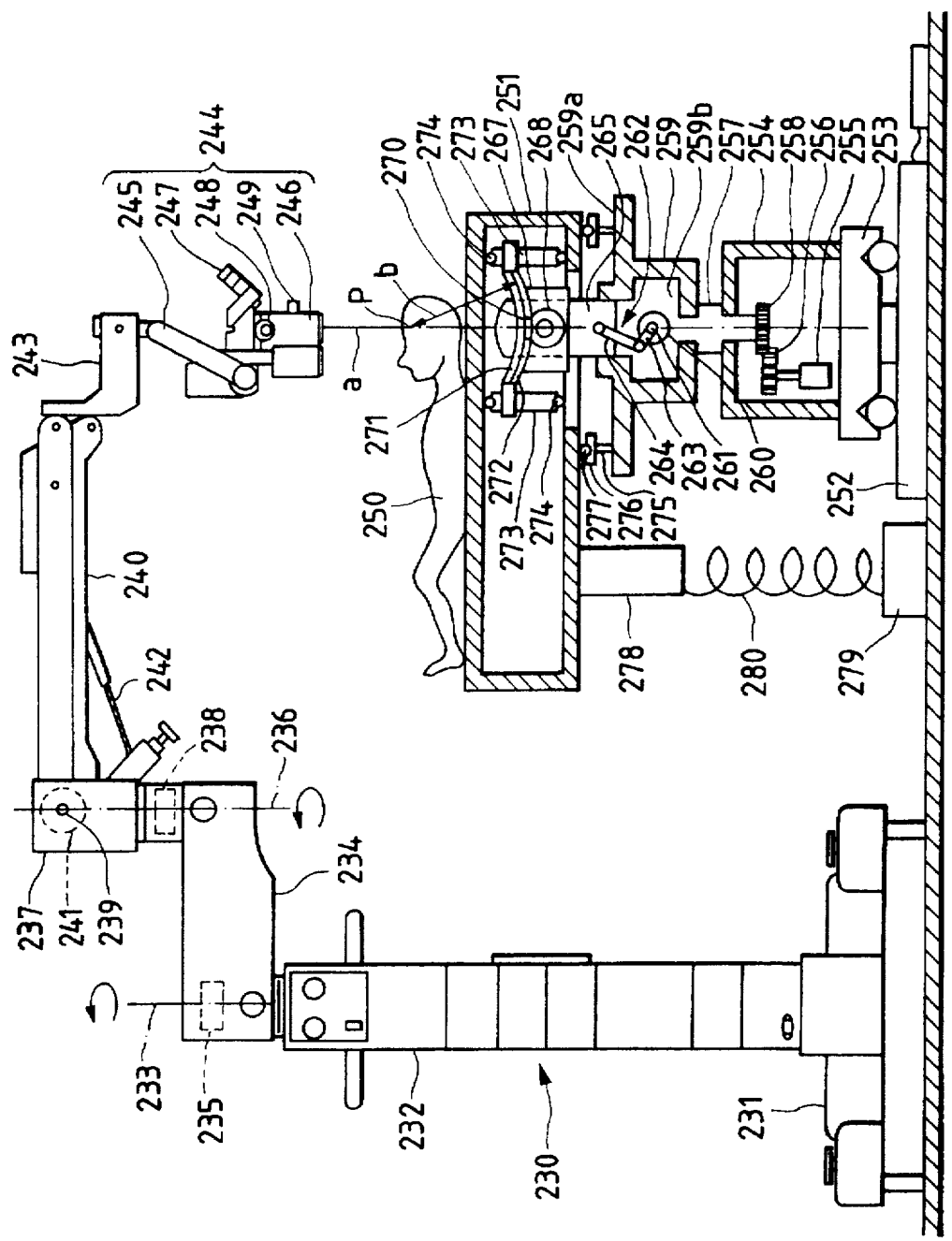
FIG. 18 is a general structural drawing of a surgical microscope according to a fifth embodiment of the invention.
Figure 19:
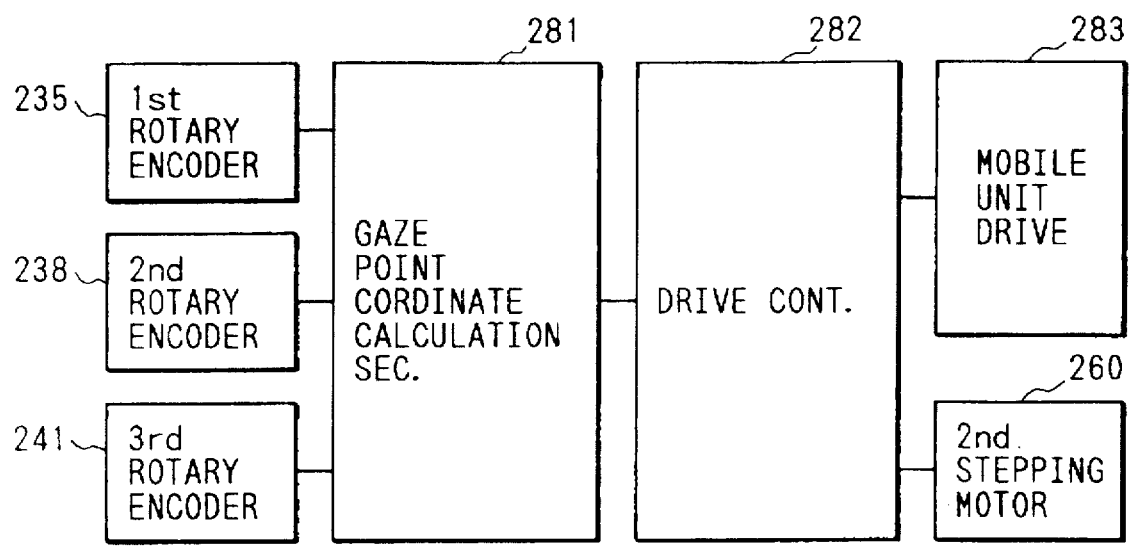
FIG. 19 is a block diagram of an electric system in the second embodiment.
Figure 20:
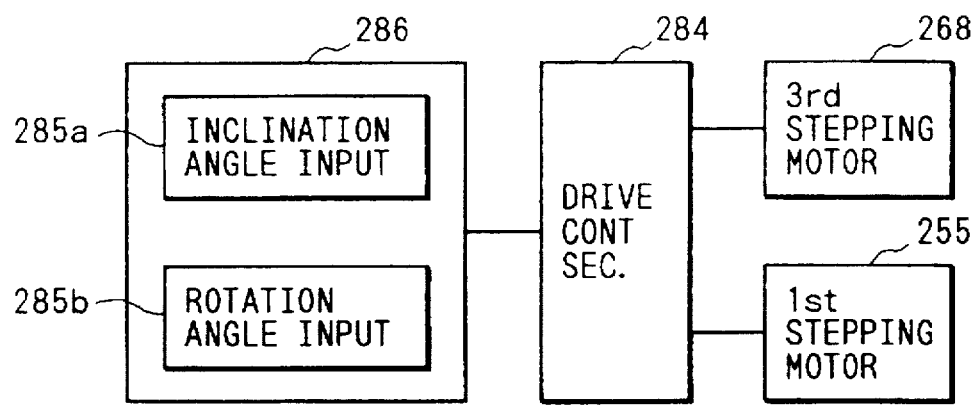
FIG. 20 is a block diagram of the electric system in the fifth embodiment.

FIGS. 18 to 20 show a fifth embodiment of the invention. FIG. 18 is a structural drawing of a surgical microscope and an operating table. FIGS. 19 and 20 are block diagrams of an electric system. As shown in FIG. 18, a base 231 of an arm rack 230 is fixed on the floor of an operating room. A strut 232 is installed upright on the base 231. A first arm 234 is rotatably supported by the strut 232 around a first rotation axis 233. The first arm 234 contains a rotary encoder 235 for detecting a rotation angle of the first arm 34 for the strut 232.

A second arm 237 is rotatably supported by the first arm 234 around a second rotation axis 236. The second arm 237 contains a rotary encoder 238 for detecting a rotation angle of the second arm 237 for the first arm 234.

A pantograph arm 240 is rotatably supported by the second arm 237 around a third rotation axis 239. The pantograph arm 240 contains a rotary encoder 241 for detecting a rotation angle of the pantograph arm 240 for the second arm 237.

The pantograph arm 240 is also supported by a gas spring 242. A microscope body section 244 is supported via an arm 243 at the tip of the pantograph arm 240. The microscope body section 244 has a microscope body 246 supported via a microscope body arm 245 by the arm 243. The microscope body 246 is provided with an eyepiece part 247, a grip 248, and a gaze point setting switch 249.

Next, an operating table 251 where a patient lies on his or her back is described. A base 252 of the operating table 251 is fixed on the floor of the operating room. Placed on the base 252 is a mobile unit 253 which has basically the same structure as in the first embodiment and can be moved by electric power in the XY directions within a horizontal plane, forming rotation drive means.

A rack 254, which is fixed on the top of the mobile unit 253, contains a first stepping motor 255 with its rotation shaft fixed in the vertical direction. A gear 256 is fitted into the rotation shaft and is meshed with a gear 258 fitted in the lower end of an operating table rotation shaft 257 supported by the rack 254 pivotally in the vertical direction.

The upper end of the operating table rotation shaft 257 projects upward from the frame 254. A horizontal mobile unit 259 having a support plate 259a in the upper part and a box 259b in the lower part is fixed to the upper end of the operating table rotation shaft 257.

The box 259b of the horizontal mobile unit 259 contains a second stepping motor 260 fixed with its rotation shaft 261 turned sideways. The rotation shaft 261 is orthogonal to the axial center of the operating table rotation shaft 257. Further, one end of a first lever 263 forming a crank mechanism 262 is fixed to the rotation shaft 261. A second lever 264 linked with the other end of the first lever 263 is linked pivotally with an elevation side plate 265 slidable up and down to the horizontal mobile unit 259.

The elevation side plate 265 is linked with a motor mounting bed 267 located in the inside at one end of the operating table 251 of a box structure. A third stepping motor 268 is fixed to the motor mounting bed 267 with its rotation shaft turned sideways. A pinion 270 is fitted into the rotation shaft and is meshed with a rack 272 of a rack plate 271 like a circular arc of radius b with the gaze point P of the part to be or being operated on as the curvature center.

Both ends of the rack plate 271 are fitted slidably up and down to guide rods 273 supported in the vertical direction within the operating table 251. Balls 274 slidable to the upper and lower faces of the inside of the operating table 251 are mounted at both upper and lower ends of the guide rods 273.

Further, a plurality of coil springs 275 are installed upright on the support plate 259a of the horizontal mobile unit 259. Rollers 277 are installed via pedestals 276 at the upper ends of the coil springs 275 for elastically supporting the lower face at one end of the operating table 251. Therefore, the horizontal mobile unit 259 can be moved horizontally along the lower face of the operating table 251. A strut 278 is projected through the lower face at the other end of the operating table 251. A coil spring 280 is disposed between the strut 278 and the base 279 fixed on the floor of the operating room.

Next, the configuration of an electric system is described with reference to FIGS. 19 and 20.

In FIG. 19, numeral 281 is a gaze point coordinate calculation section which inputs signals from the first to third rotary encoders 235, 238, and 241 and the gaze point setting switch 249 and calculates three-dimensional coordinates of a gaze point position at which the operator observes. Numeral 282 is a drive control section outputs drive signals to a mobile unit drive section 283 and the second stepping motor 260 in response to a signal from the gaze point coordinate calculation section 281.

In FIG. 20, numeral 284 is a drive control section which inputs a signal from a foot switch 286 comprising an operating table inclination angle input section 285a which inputs the angle at which the operating table 251 is inclined with the gaze point P as the center and an operating table rotation angle input section 285b which inputs the angle at which the operating table 251 is rotated with the gaze point P as the center, and outputs drive signals to the first stepping motor 255 and the third stepping motor 268.

Next, the operation of the surgical microscope having the structure described above is discussed.

First, before an operation on a patient 250, the patient 250 is fixed at any desired position on the operating table 251. When starting the operation and using the surgical microscope, the operator moves the microscope body section 244 by horizontally rotating the first arm 234 and focuses the microscope body 246 on the part to be operated on by moving the pantograph arm 240 up and down for observation.

When the operator presses the gaze point setting switch 249, the gaze point coordinate calculation section 281 calculates the three-dimensional coordinates of the gaze point and the drive control section 282 outputs a drive signal to the mobile unit drive section 283 for horizontally moving the mobile unit 253 so that the axial center of rotation of the operating table rotation shaft 257 and the optical axis a of the microscope body 246 become coaxial. When the drive control section 282 outputs a drive signal to the second stepping motor 260 for rotating the rotation shaft 261 so that the circular arc of the rack 272 matches the position at a distance of b from the gaze point P, the pinion 270 fixed to the elevation side plate 265 via the crank mechanism 262 is moved up and down for moving the rack 272.

Next, an example in which the operator changes the observation angle and direction for observation at the gaze point P is discussed. The operator enters a desired observation angle through the operating table inclination angle input section 285a of the foot switch 286. The drive control section 284 outputs a drive signal to the third stepping motor 268 for rotating the pinion 270 for moving the rack 272.

thereby expanding or shrinking the coil springs 275 and 280 for inclining the operating table 251 with the gaze point as the center for observation.

Likewise, the operator enters a desired observation direction through the operating table rotation angle input section 285b of the foot switch 286. The drive control section 284 outputs a drive signal to the first stepping motor 255 for rotating the operating table rotation shaft 257 by the gears 256 and 258, thereby rotating the operating table 251 with the gaze point P as the center for observation.

According to the fifth embodiment, if the operator focuses the microscope body 201 on the part to be or being operated on and turns on the gaze point setting switch 249, automatically the rotation center point of the operating table 251 moves to the gaze point P of the microscope body 201. Thus, the operator can change the observation angle and direction by electric power with operating instruments held by both hands without changing an eyepoint, thus can take treatment in an easy attitude and need not stop the operation to change the observation angle or direction, shortening the operating time.

Incidentally, it is possible to input the calculation result of the distance calculation circuit 103 (shown in FIG. 16) to the gaze point calculation section 281 for the mode in which the microscope body is not moved but the patient (i.e., bet) is moved.

FIGS. 21 to 26 show a third embodiment of the invention. The sixth embodiment provides a surgical microscope which attaches importance to operability at key hole surgery performed increasingly as a low invasion operation. At present, an opening of patient's cranium is made as small as possible in an operation for a change to a morbid state in the cranium aiming at a low invasion in cerebral surgery. Therefore, a change to a morbid state at the deep part of the cranium must be able to be observed even through the small opening of the cranium.

Figure 21:
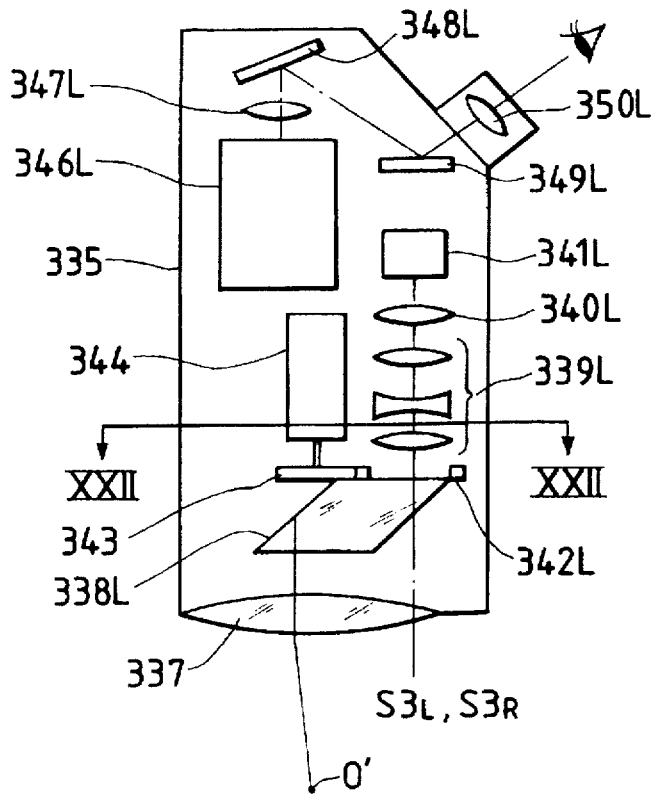
FIG. 21 is a drawing showing the internal structure of a microscope body according to a sixth embodiment of the invention.
Figure 22:
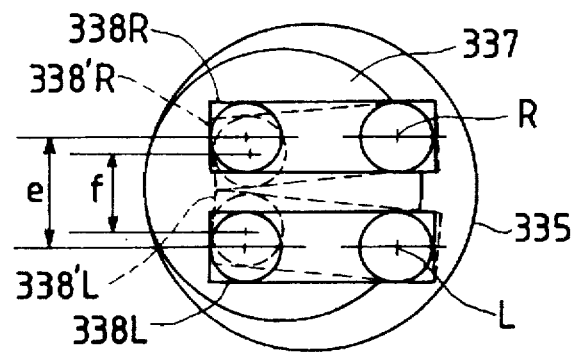
FIG. 22 is a drawing showing an optical layout taken on line XXII—XXII of FIG. 21.
Figure 23:
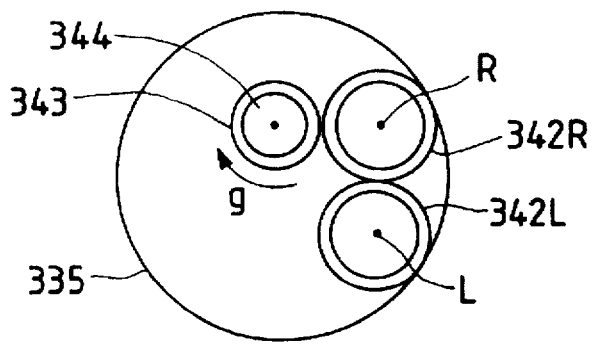
FIG. 23 is a drawing showing a mechanical layout taken on line XXII—XXII of FIG. 21.
Figure 24:
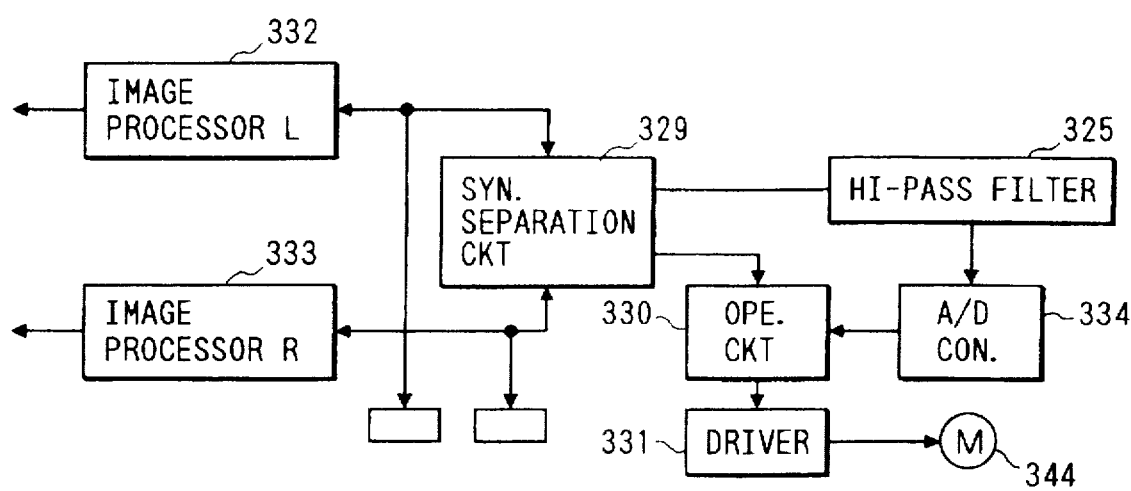
FIG. 24 is a block diagram showing an electric system in the third embodiment.
Figure 25:
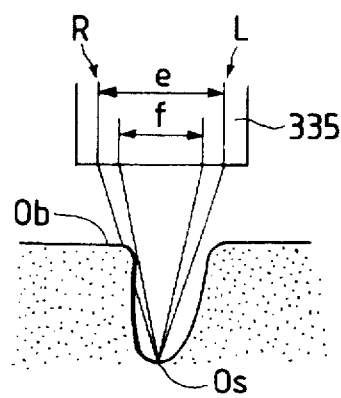
FIG. 25 is a drawing showing the relationship of spacings between optical axes in the third embodiment.

FIG. 21 is a drawing showing the internal structure of a microscope body 335. FIG. 22 is a drawing showing an optical layout taken on line XXII—XXII of FIG. 21. FIG. 23 is a drawing showing a mechanical layout taken on line XXII—XXII of FIG. 21. FIG. 24 is a block diagram showing an electric system. FIG. 25 is a drawing showing the relationship of optical axis intervals. FIG. 26 is drawings showing the relationship with picture signal.

The microscope body 335 is described with reference to FIGS. 21 and 22. The microscope body 335 has an object lens 338 common to left and right observation optical paths, only one of which is shown. Each of the left and observation optical paths is formed with parallel prisms 338L, 338R, a magnification change optical system 339 driven by a drive mechanism (not shown), and an imaging lens 340L. An image pick-up section 341L made of CCD is located at each imaging position of the imaging lens 340L.

Further, a display 346L for left and right eyes for displaying an image formed by the image pick-up section 341L, an image processor L 332, and an image processor R 333 is installed. A lens 347L, a microscope body 348L, a microscope body 349L, and an eyepiece 350L are disposed on each optical path.

As shown in FIG. 23, gears 342L and 342R are fixed to the parallel prisms 338L and 338R; they are mounted pivotally with the observation optical axis centers L and R as the rotation centers. Further, the gears 342L and 342R fixed to the parallel prisms 338L and 338R are meshed together and the gear 342R meshes with a gear 343 fixed to the rotation shaft of a motor 344.

The configuration of an electric system is described with reference to FIG. 24. The image processor L 332 consists of a drive circuit (not shown) for driving the CCD of the image pick-up section 341L and reading data and a picture signal processing circuit (not shown) for generating a picture signal from an output signal of the drive circuit. The image processor L 332 is connected to the display 346L contained in the microscope body 335 and a synchronous separation circuit 329. The image processor R 333 is similar to the image processor L 332 and therefore will not be discussed again. The synchronous separation circuit 329 is adapted to synchronously run the image processors L 332 and R 333 and separate horizontal and vertical synchronizing signals; synchronizing signals are output to an operation circuit 330 and 2-system picture signals are output via a high-pass filter 325 and an A/D conversion circuit 334 to the operation circuit 330. An operation output of the operation circuit 330 is fed into a driver 331, which is a drive circuit of the motor 344.

In operation, left and right observation images formed by the object lens 337, the parallel prisms 338L and 338R, the magnification change optical system 339L, and the imaging lens 340L are imaged by the image pick-up section 341L and the image processors L 332 and R 333 for displaying on the display 346L. The image passed through the left observation optical path is displayed on the display 346L and the image passed through the right observation optical path is displayed on another display (not shown). The operator observes the image on the display 346L via the eyepiece 350L and the microscope bodies 349L and 348L by left eye and the image on the display (not shown) via the eyepiece and the microscope bodies by right eye for stereoscopic observation.

Figure 26A:
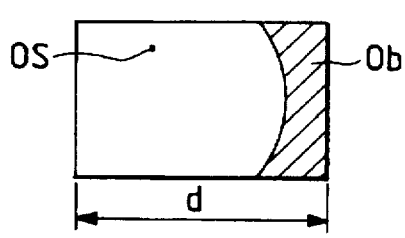
FIGS. 26a and 26b are drawings showing the relationship with picture signal in the third embodiment.
Figure 26B:
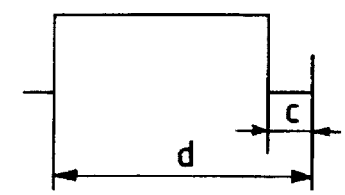

Now, assume that the operator observes a change part to a morbid state at the deep part in a body cavity, Os, through an opening of the body surface, Ob, at the part to be or being operated on. At the time, the spacing between the left and right observation optical axes in the microscope body 335 is e shown in FIGS. 22 and 25. As shown in FIG. 25, at the right observation optical path, the opening Ob blocks a part of flux of light, resulting in an image shown in FIG. 26a. The image corresponding to the opening Ob, which is a blur image, is cut through the high-pass filter 325, and an output from the A/D conversion circuit 334 becomes as shown in FIG. 26b. The operation circuit 330 detects the part c and drives the motor 344 via the driver 331 so as to eliminate it.

As the motor 344 rotates, the gear 343 is pivoted in the direction of g shown in FIG. 23 and further the parallel prisms 338L and 338R are pivoted to positions 338L' and 338R' by the gears 342L and 342R. In the state, the spacing between the left and right observation optical axes becomes f shown in FIGS. 22 and 25 and the opening Ob doe s not block flux of light for observation.

Therefore, stereoscopic observation in various directions through a small opening is also enabled in key hole surgery aiming at a low invasion in recent years and adjustment therefor is made automatically during the operation, thus the operator can more concentrate on the operation, leading to smooth progress of surgery.

As described above, according to the invention, the mechanism for changing the observation angle and direction with the gaze point as the center is disposed at a position distant from the microscope body, thus does not disturb the operator who handles the microscope body and performs the operation and also enables the operator to easily observe the part to be or being operated on at every angle from every direction for improving operability.

What is claimed is:

1. A surgical microscope system having a microscope body comprising:

an observation optical system capable of changing an observation direction with a point on an observation optical axis of the microscope body as a swivel center, an observation focal point of said observation optical system being movable relative to said swivel center;

focal point position movement control means for moving the focal point for identifying the focal position of the microscope body with the swivel center;

focal position detecting means for detecting the focal point position of the microscope body;

control means for storing a signal representative of a reference focal point position which is generated by said focal position detecting means and used as a reference and for comparing said reference focal point position with an output from said focal point position detecting means; and focal point position moving means for moving the focal point position on the basis of an output of said control means.

2. The surgical microscope system according to claim 1, wherein said focal point position detecting means further comprises:

a focal distance variable objective lens disposed in said observation optical system of said microscope body; and lens position detecting means connected to said variable objective lens for detecting a position of a lens which constitutes said variable objective lens.

3. A surgical microscope system having a microscope body comprising:

an observation optical system capable of changing an observation direction with a point on an observation optical axis of the microscope body as a swivel center, an observation focal point of said observation optical system being movable relative to said swivel center;

a spherical concave member and a spherical convex member which are slidable relative to each other about the swivel center and which are disposed opposite said microscope body with respect to the swivel center; and an arm for connecting said spherical convex member and said microscope body so that the focal point position of said microscope body corresponds to the swivel center.

4. A surgical microscope system having a microscope body comprising:

an observation optical system capable of changing an observation direction with a point on an observation optical axis of the microscope body as a swivel center, an observation focal point of said observation optical system is movable relative to said swivel center;

object position detecting means for detecting a three-dimensional coordinate of an object positioned at a view center of the microscope body;

swivel center defining means for defining the swivel center on the basis of an output of said object position detecting means; and drive means for moving said swivel center defining means in a three-dimensional manner.

5. The surgical microscope system according to claim 4, wherein said swivel center defining means includes a parallel link mechanism for supporting said microscope body.

6. The surgical microscope system according to claim 4, wherein said swivel center defining means includes an arcuate rack plate disposed on an operation surface for supporting a patient.

7. The surgical microscope system according to claim 4, further comprising:

a control circuit for comparing the output from said swivel center position defining means with the output from said object position detecting means and said control means, wherein said drive means are moved by outputs generated by said swivel center defining means.

* * * * *